(12) United States Patent
Kasagi et al.

(10) Patent No.: US 8,912,010 B2
(45) Date of Patent: Dec. 16, 2014

(54) THYROXINE IMMUNOASSAY USING FLUORESCENT PARTICLES

(75) Inventors: Noriyuki Kasagi, Ashigarakami-gun (JP); Junichi Katada, Ashigarakami-gun (JP); Tadahiro Matsuno, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/610,497

(22) Filed: Sep. 11, 2012

(65) Prior Publication Data

US 2013/0078737 A1    Mar. 28, 2013

(30) Foreign Application Priority Data

Sep. 26, 2011  (JP) ................................. 2011-208526
Aug. 31, 2012  (JP) ................................. 2012-191028

(51) Int. Cl.
*G01N 33/544* (2006.01)
*G01N 33/53* (2006.01)
*C07K 1/04* (2006.01)
*G01N 33/543* (2006.01)
*G01N 33/78* (2006.01)
*G01N 33/58* (2006.01)

(52) U.S. Cl.
CPC .......... *G01N 33/54373* (2013.01); *G01N 33/78* (2013.01); *G01N 33/54306* (2013.01); *G01N 33/585* (2013.01)
USPC ............ 436/528; 435/7.92; 435/7.1; 530/403

(58) Field of Classification Search
CPC .................... A61K 47/48284; A61K 47/4833; G01N 33/78; G01N 33/54306; G01N 33/54373
See application file for complete search history.

(56) References Cited

U.S. PATENT DOCUMENTS

| 4,110,076 A | 8/1978 | Margherita |
| 4,243,749 A * | 1/1981 | Sadeh et al. ................. 435/7.92 |
| 4,735,907 A | 4/1988 | Schaeffer et al. |
| 2002/0027133 A1 | 3/2002 | Kellogg et al. |
| 2009/0261269 A1 | 10/2009 | Horii et al. |

FOREIGN PATENT DOCUMENTS

| GB | 1540728 | 2/1979 |
| JP | 51106724 A | 9/1976 |
| JP | 58174851 A | 10/1983 |
| JP | 62142275 A | 6/1987 |
| JP | 6-94709 A | 4/1994 |
| JP | 7-146293 A | 6/1995 |
| JP | 2003270252 A | 9/2003 |
| JP | 2008-249361 A | 10/2008 |
| JP | 2010032283 A | 2/2010 |
| JP | 2010-190880 A | 9/2010 |

OTHER PUBLICATIONS

Gobi et al., High sensitive regenerable immunosensor for label-free detection of 2,4-dichlorophenoxyacetic acid at ppb levels by using surface plasmon resonance imaging., Sensors and Actuators B, 2006, vols. 111-112, pp. 562-571.*
Notice of Reasons for Rejection, dated Aug. 20, 2013, issued in corresponding JP Application No. 2012-191028, 5 pages in English and Japanese.
Communication, dated Dec. 6, 2012, issued in corresponding EP Application No. 12184486.4, 6 pages.
Ali et al., "Generation and establishment of hybridoma clones producing monoclonal antibodies against thyroxine hormone (T4)," Malaysian Applied Biology, vol. 24, No. 2, 1995, pp. 81-88, XP008158342.

* cited by examiner

*Primary Examiner* — Shafiqul Haq
(74) *Attorney, Agent, or Firm* — Sughrue Mion, PLLC

(57) ABSTRACT

Provided are a base plate and a method for thyroxine immunoassay, which are capable of decreasing the signal change rate caused by temperature change in a high-sensitivity immunoassay method for thyroxine. A base plate for thyroxine immunoassay which has a conjugate of thyroxine or a derivative thereof and albumin immobilized thereon, and in which the ratio of the molecule number of thyroxine or a derivative thereof to the molecule number of albumin in the immobilized conjugate, is disclosed.

5 Claims, 1 Drawing Sheet

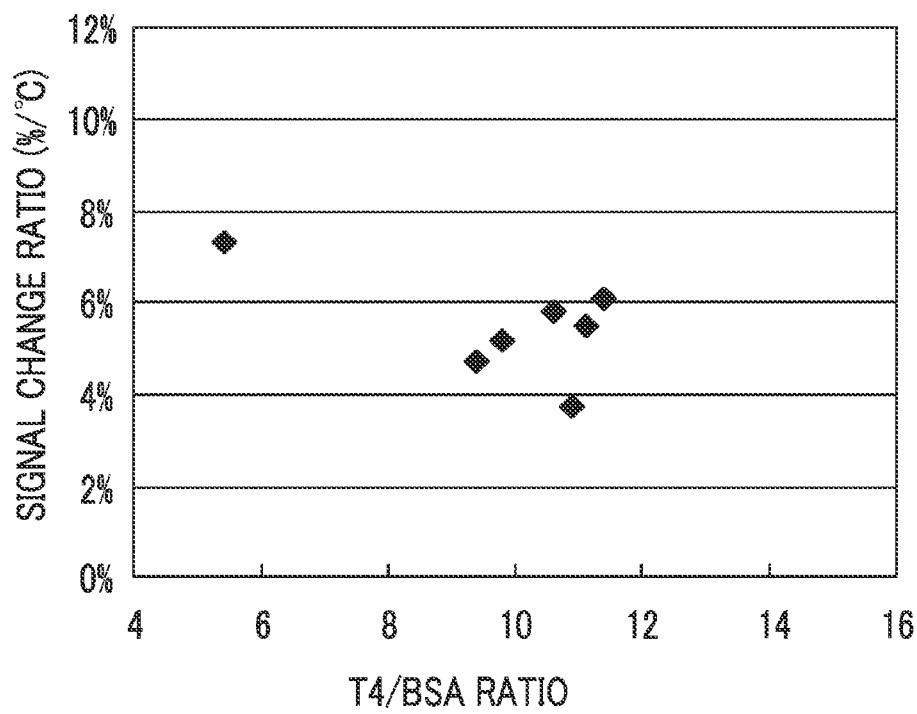

THYROXINE IMMUNOASSAY USING FLUORESCENT PARTICLES

BACKGROUND OF THE INVENTION

1. Field of the Invention

The present invention relates to a base plate and a method for immunoassay of thyroxine using fluorescent particles.

2. Description of the Related Art

Fluorescence detection methods have been hitherto used in a large variety of fields, as analytic methods that are highly sensitive and simple and are capable of quantitatively determining proteins, enzymes, inorganic compounds and the like. These fluorescence detection methods are methods by which a sample which is suspected to contain a substance to be detected (test substance) that is excited by light having a specific wavelength and emits fluorescence, is irradiated with excitation light having the specific wavelength, fluorescence is detected at that time, and thereby the presence of the test substance is verified. Furthermore, in the case where the substance is not a fluorescent material, a method of bringing a substance which specifically binds to a test substance labeled with a fluorescent dye, into contact with a sample, subsequently detecting fluorescence in the same manner as described above, and thereby verifying the presence of this binding, that is, the presence of the test substance, is also widely used.

In regard to such fluorescent detection methods, a method of utilizing the effect of electric field reinforcement by plasmon resonance so as to increase the sensitivity of detection, is known. In such a method, in order to induce plasmon resonance, a sensor chip in which a metal layer is provided in a predetermined region on a transparent support is prepared, and excitation light is caused to enter the sensor chip through the surface of the support on the opposite side of the metal layer-formed surface with respect to the interface between the support and the metal film, at a predetermined angle that is greater than or equal to the total reflection angle. Irradiation of such excitation light causes generation of surface plasmon at the metal layer. Through the electric field reinforcing action brought by the generation of such surface plasmon, fluorescence is reinforced, and thereby the signal/noise ratio (S/N ratio) is increased. In a fluorescence detection method involving surface plasmon excitation (hereinafter, referred to as "SPF method"), the degree of signal reinforcement can be about 10 times, and analysis can be conducted with high sensitivity, as compared to a fluorescence detection method involving epi-illumination excitation (also called epi-illumination fluorescence method).

For example, in the light signal detection method for determining the amount of a test substance as described in JP 2010-190880 A, a sensor chip which has a sensor unit including a metal layer, provided in a predetermined region of one surface of a dielectric plate is prepared, and the sensor unit of the sensor chip is brought into contact with a sample. Through such contact, a binding substance attached with a photoresponsive labeling substance in an amount equivalent to the amount of the test substance contained in the sample, binds to the sensor unit. Subsequently, excitation light is irradiated to the predetermined region, and light from the photoresponsive labeling substance, which is produced in the electric field-reinforced field produced on the metal layer, is detected. Thus, the amount of the test substance can be determined. Furthermore, in this method, it is also possible to use, as a photoresponsive labeling substance, a light transmitting material which transmits the light produced from a photoresponsive substance, and in which plural photoresponsive substances are included such that the metal quenching occurring when the photoresponsive substances approach the metal layer is prevented.

Thyroxine (T4; also called thyroxin) is one kind of thyroid hormones secreted from the thyroid gland. Generally, thyroxine acts on cells of the whole body and has a function of increasing the metabolic rate of cells. Known examples of thyroid hormones include thyroxine (T4) and triiodothyronine (T3), but a majority of the thyroid hormones circulating in the blood is thyroxine (T4). As a method for measuring this thyroxine, an enzymatic immunoassay method which involves simple operation has been conventionally known. For example, JP 1995-146293 A (JP-H-07-146293 A) discloses an enzymatic immunoassay method utilizing a competition method for measuring the amount of thyroxine, and describes an enzymatic immunoassay method using magnetic microbeads for the purpose of shortening the enzymatic reaction time. Furthermore, JP 1994-094709 A (JP-H-06-094709 A) discloses an enzymatic immunoassay method and a reagent for measuring free thyroxine as a free thyroid hormone, and describes an enzymatic immunoassay method and a reagent which us a specific labeled enzyme for the purpose of suppressing the influence of albumin in blood.

SUMMARY OF THE INVENTION

As mentioned above, methods for immunoassay of thyroxine have been traditionally available. However, since enzymatic reactions exhibit high temperature dependency, to carry out strict temperature management at the time of reaction is necessary. Therefore, an object to be solved by the present invention is to provide a convenient immunoassay method for thyroxine with high sensitivity, which is capable of decreasing the signal change rate due to temperature change, and a base plate to be used for immunoassay.

The inventors of the present invention conducted a thorough investigation to solve the problems described above, and as a result, they found that the signal change rate caused by temperature change can be decreased in the immunoassay of thyroxine, by using a base plate on which a conjugate obtained by conjugating thyroxine or a thyroxine derivative with albumin at certain proportions is immobilized, bringing this base plate into contact with anti-thyroxine antibody-labeled fluorescent particles and thyroxine as a test substance, so as to cause the thyroxine on the base plate (thyroxine in the conjugate of thyroxine or a derivative thereof with albumin) and the thyroxine as a test substance to competitively bind to the anti-thyroxine antibody-labeled fluorescent particles, and thereby measuring the fluorescence based on the anti-thyroxine antibody-labeled fluorescent particles bound to the base plate. The present invention was accomplished based on these findings.

According to an aspect of the present invention, there is provided a base plate for thyroxine immunoassay on which a conjugate of thyroxine or a derivative thereof and albumin having a thyroxine or derivative thereof/albumin ratio of from 8 to 12 is immobilized. According to another aspect of the present invention, there is provided a conjugate of thyroxine or a derivative thereof and albumin having a thyroxine or derivative thereof/albumin ratio of from 8 to 12.

According to another aspect of the present invention, there is provided a method for measuring thyroxine in a test sample, the method including: (1) a step of bringing anti-thyroxine antibody-labeled fluorescent particles and a test sample containing thyroxine into contact with a base plate for thyroxine immunoassay on which a conjugate of thyroxine or a derivative thereof and albumin having a thyroxine or derivative thereof/albumin ratio of from 8 to 12 is immobilized; and (2) a step of measuring the fluorescence based on the anti-thyroxine antibody labeled fluorescent particles bound to the base plate. According to still another aspect of the present invention, there is provided a conjugate of thyroxine or a derivative thereof and albumin having a thyroxine or derivative thereof/albumin ratio of from 7 to 12.

Preferably, the albumin is bovine serum albumin.

Preferably, in the step (2), fluorescence is measured by surface plasmon fluorescence measurement or epi-illumination fluorescence measurement.

According to the present invention, the signal change rate caused by temperature change in the immunoassay of thyroxine can be decreased.

BRIEF DESCRIPTION OF THE DRAWINGS

FIG. 1 is a diagram illustrating the relationship between the signal change rate caused by temperature change and the labeling index of T4-BSA, which is shown in Table 2 for the Example of the present invention.

DESCRIPTION OF THE PREFERRED EMBODIMENTS

Hereinafter, the present invention will be described in more detail.

The present invention relates to a conjugate of thyroxine or a derivative thereof and albumin having a thyroxine or derivative thereof/albumin ratio of from 8 to 12, a base plate for thyroxine immunoassay on which the conjugate is immobilized, and a method for measuring thyroxine in a test sample, the method including: (1) a step of bringing anti-thyroxine antibody-labeled fluorescent particles and a test sample containing thyroxine into contact with the base plate; and (2) a step of measuring the fluorescence based on the anti-thyroxine antibody labeled fluorescent particles bound to the base plate.

(Thyroxine (T4))

Thyroxine is a compound having the following structure (hereinafter, in the present invention, thyroxine may be abbreviated to T4).

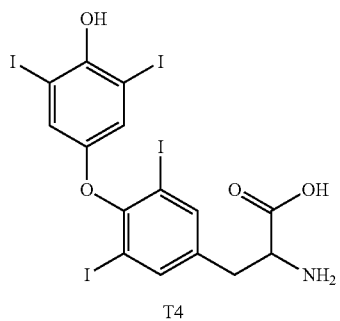

[Chem. 1]

T4

Furthermore, a derivative of thyroxine may be a compound modified with an appropriate functional group of thyroxine, such as a carboxyl group or an amino group. Specific examples of the derivative of thyroxine (T4) include compounds obtained by esterifying the carboxyl group of thyroxine. Furthermore, the amino group of thyroxine may be bonded to a linker having a carboxyl group on the end on the opposite side of the end that reacts with the amino group, if necessary. The structure of a specific example of a thyroxine derivative obtained by esterifying the carboxyl group of thyroxine is shown below.

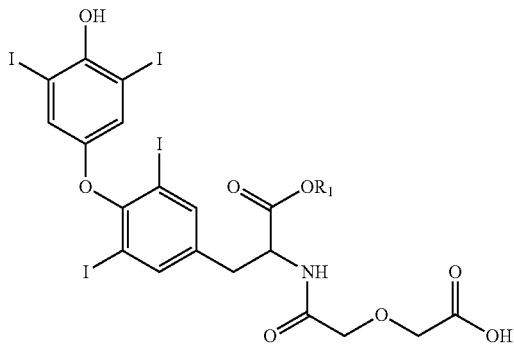

[Chem. 2]

Specific example of T4 derivative
$R_1$ = H, methyl, ethyl, n-propyl, i-propyl, t-butyl (Albumin)

The type of albumin used in the present invention is not particularly limited, but for example, albumin derived from an animal (cattle, human being or the like), preferably a serum albumin derived from an animal (cattle, human being or the like), and particularly preferably bovine serum albumin (in the present invention, may be abbreviated to BSA) can be used.

(Conjugate of Albumin and Thyroxine or Derivative Thereof)

The present invention provides a base plate for thyroxine immunoassay on which a conjugate of thyroxine or a derivative thereof and albumin having a ratio of the molecule number of thyroxine or a derivative thereof to the molecule number of albumin of from 8 to 12, is immobilized. The ratio of the molecule number of thyroxine or a derivative thereof to the molecule number of albumin in the conjugate of the present invention is from 8 to 12, preferably from 9 to 12, even more preferably from 9 to 11, and most preferably from 9 to 10.

The ratio of molecule number of thyroxine or a derivative thereof to the molecule number of albumin means the ratio of molecule numbers (mole number), and means the number of molecules of thyroxine (T4) or a derivative thereof bound to one molecule of albumin (BSA or the like) (hereinafter, briefly indicated as thyroxine or derivative thereof/albumin ratio). The thyroxine or derivative thereof/albumin ratio can be determined by, for example, matrix-assisted laser desorption-ionization time-of-flight mass spectrometry (MALDI-TOF-MS), and the specific procedure of measurement is as follows. A sample is dissolved in 0.1 mass % trifluoroacetic acid (TFA):acetonitrile (ACN)=2/1, and the concentration is adjusted to 1 mg/mL. 4 μL of a matrix (sinapinic acid (SA)) and 1 μL of the sample are mixed, and the mixture is spot-applied in 1 μL×4 spots on a gold plate. Thereafter, the sample is naturally dried. The gold plate is inserted into a MALDI-TOF-MS apparatus (Voyager manufactured by Applied Bio Systems, Inc.), and measurement is carried out. Accumulated data of 900 shots are obtained from each spot (N=4). In regard to a peak corresponding to the conjugate of thyroxine or a derivative thereof and albumin, the position vertically drawn from the center of the area of the part which exhibits an intensity of 50% or greater of the maximum value of the peak intensity of the peak is designated as the molecular weight of the conjugate of thyroxine or a derivative thereof and albumin, and the average value of N=4 is used to calculate the number of bound molecules according to the formula: (molecular weight of the conjugate of thyroxine or derivative thereof and albumin−molecular weight of native BSA)/molecular weight of T4 derivative (when the albumin is BSA, 906-18=888).

The conjugate of thyroxine or a derivative thereof and albumin of the present invention is such that thyroxine or a derivative thereof and albumin may be directly bonded, or may be bonded via an appropriate linker. For example, as will be described in the following Examples, a conjugate of thyroxine or a derivative thereof and albumin can be prepared by producing a thyroxine derivative having a carboxyl group, activating this carboxyl group by using 1-ethyl-3-(3-dimethylaminopropyl)carbodiimide hydrochloride (WSC), N-hydroxysuccinimide (NHS) and the like, and bonding the activated carboxyl group to the amino group of albumin.

The thyroxine or derivative thereof/albumin ratio in the conjugate of the present invention can be regulated by adjusting the reaction conditions for the bonding reaction between thyroxine or a derivative thereof and albumin (the use amounts of thyroxine and albumin, and the like). The aforementioned adjustment can be carried out by making reference to the literature (Bioconjugate Chem., 1994, 4, 419-424).

It is known that when the thyroxine or derivative thereof/albumin ratio increases, the solubility in a solvent such as water decreases. In the present invention, in practice, when the thyroxine or derivative thereof/albumin ratio is greater than 12, a decrease in solubility is confirmed. In that case, there is a risk for a decrease in the accuracy of immunoassay. On the other hand, when the thyroxine or derivative thereof/albumin ratio is less than 8, the signal change rate caused by temperature change increases, the performance of immunoassay is deteriorated, and the effect of the present invention cannot be achieved.

(Base Plate)

In the present invention, a base plate for thyroxine immunoassay is provided by immobilizing the above-described conjugate of thyroxine or a derivative thereof and albumin having a thyroxine or derivative thereof/albumin ratio of from 8 to 12, to a base plate. The type of the base plate is not particularly limited so long as the base plate is capable of the fluorescence analysis that will be described below, and a base plate of any material can be used. The conjugate of thyroxine or a derivative thereof and albumin can be bonded to the base plate by a method of dissolving the conjugate in a buffer solution, spot-applying the solution onto the base plate, leaving the solution to stand for a certain time, subsequently suctioning the supernatant, and drying the residue.

In the case of performing a surface plasmon fluorescence detection method (SPF method) that will be described below, regarding the base plate, it is preferable to use a base plate having a metal film on the surface. The metal that forms the metal film is not particularly limited so long as the metal is capable of producing surface plasmon resonance. Preferred examples thereof include free-electron metals such as gold, silver, copper, aluminum, and platinum, and gold is particularly preferred. Those metals can be used individually or in combinations. Furthermore, in consideration of the adhesiveness to the base plate, an intermediate layer formed from chromium or the like may be provided between the base plate and the layer formed of a metal. The thickness of the metal layer is not limited, but for example, the thickness is preferably from 0.1 nm to 500 nm, and particularly preferably from 1 nm to 200 nm. When the thickness is greater than 500 nm, the surface plasmon phenomenon of the medium cannot be sufficiently detected. Also, in the case of providing an intermediate layer formed from chromium or the like, the thickness of the intermediate layer is preferably from 0.1 nm to 10 nm.

Formation of the metal film may be carried out according to a routine method, and can be carried out by, for example, a sputtering method, a vapor deposition method, an ion plating method, an electroplating method, or an electroless plating method.

The metal film is preferably disposed on the base plate. Here, the term "disposed on the base plate" includes the case where the metal film is disposed on the base plate so as to be in direct contact, as well as the case where the metal film is disposed over the base plate without being in direct contact with the base plate, with another layer interposed between the metal film and the base plate. Regarding the base material that can be used in the present invention, for example, in the case of using the base plate for a surface plasmon resonance biosensor, a material which is transparent to laser light, such as optical glass such as BK7 (borosilicate glass), which is one kind of general optical glass, or a synthetic resin, specifically, polymethyl methacrylate, polyethylene terephthalate, polycarbonate or a cycloolefin polymer, can be used. For such a base plate, preferably, a material which does not exhibit anisotropy to polarized light and has excellent processability is desirable. According to the present invention, an embodiment in which the conjugate of thyroxine or a derivative thereof and albumin is immobilized onto the metal film, is preferred.

A preferred example of the base plate for SPF detection may be a base plate obtained by vapor depositing a gold film on a base plate based on polymethyl methacrylate (PMMA).

Furthermore, according to the present invention, thyroxine in a test sample can be measured by bringing the base plate for thyroxine immunoassay of the present invention described above, into contact with anti-thyroxine antibody-labeled fluorescent particles and a test sample containing thyroxine, and then measuring the fluorescence based on the anti-thyroxine antibody-labeled fluorescent particles bound to the conjugate of thyroxine or a derivative thereof and albumin on the base plate.

(Fluorescent Particles)

Particles colored with a fluorescence that can be conventionally used in an immune reaction can be used as the fluorescent particles to be used in the present invention, and for example, fluorescent polymer particles such as fluorescent polystyrene beads, and fluorescent glass particles such as fluorescent glass beads can be used. Specific examples of the material of the fluorescent particles include synthetic polymer powders of polymers using monomers such as styrene, methacrylic acid, glycidyl(meth)acrylate, butadiene, vinyl chloride, vinyl acetate acrylate, methyl methacrylate, ethyl methacrylate, phenyl methacrylate, and butyl methacrylate; and copolymers using two or more monomers. Latexes obtained by uniformly suspending these synthetic polymer powders are preferred. Further examples include organic polymer powders, inorganic substance powders, microorganisms, blood corpuscles, cellular membrane fragments, and liposomes.

In the case of using latex particles, specific examples of the latex material include polystyrene, a styrene-acrylic acid copolymer, a styrene-methacrylic acid copolymer, a styrene-glycidyl(meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and polyvinyl acetate acrylate. The latex is preferably a copolymer containing at least styrene as a monomer, and particularly preferably a copolymer of styrene with acrylic acid or methacrylic acid. The method for producing the latex is not particularly limited, and the latex can be produced by any polymerization method. However, if a surfactant is present at the time of antibody labeling, antibody immobilization is not easily achieved. Therefore, for the production of the latex, emulsifier-free emulsion polymerization, that is, emulsion polymerization in which no emulsifier such as surfactant is used, is preferred.

When the latex which is obtained by polymerization is fluorescent per se, the latex can be used directly as fluorescent latex particles. When the latex obtained by polymerization is non-fluorescent, fluorescent latex particles can be produced by adding a fluorescent substance (a fluorescent dye or the like) to the latex. That is, fluorescent latex particles can be produced by adding a fluorescent dye to a solution of latex particles containing water and a water-soluble organic solvent, and stirring the mixture.

The average particle size of the fluorescent particles may vary with the material of the particles, the concentration range for the quantitative determination of the test substance, the measuring instrument, and the like; however, the average particle size is preferably in the range of 0.001 μM to 10 μm (more preferably 0.001 μm to 1 μn). Liposomes or microcapsules containing a fluorescent dye can also be used as fluorescent particles. The fluorescence emission color is not particularly limited so long as the color is to be emitted when the fluorescent substance is excited by absorbing ultraviolet radiation or the like, and returns to the ground state, and for example, fluorescence emission colors such as yellow-green (excitation wavelength: 505 nm/emission wavelength: 515 nm; hereinafter, the same), blue (350 nm to 356 nm/415 nm to 440 nm), red (535 nm to 580 nm/575 nm 605 nm), orange (540 nm/560 nm), red-orange (565 nm/580 nm), crimson (625 nm/645 nm), and dark red (660 nm/680 nm) can be used. Fluorescent particles emitting these fluorescence spectra are available from, for example, Invitrogen, Inc., and those fluorescent particles are commercially available under the trade name FluoSpheres (registered trademark) from the same company.

(Method for Measuring Average Particle Size)

The average particle size of the fluorescent particles used in the present invention can be measured with a commercially available particle size distribution analyzer or the like. Known examples of the measurement methods for particle size distribution include optical microscopy, confocal laser microscopy, electron microscopy, atomic force microscopy, static light scattering, laser diffraction, dynamic light scattering, centrifugal sedimentation, electric pulse measurement, chromatography and ultrasonic attenuation, and apparatuses corresponding to the various principles are commercially available.

In view of the particle size range and the ease of measurement, a dynamic light scattering method can be preferably used in the present invention. Examples of commercially available measuring apparatuses using dynamic light scattering include NanoTrack UPA (Nikkiso Co., Ltd.), a dynamic light scattering type particle size distribution analyzer, LB-550 (Horiba, Ltd.), and a concentrated system particle size analyzer, FPAR-1000 (Otsuka Electronics Co., Ltd.). In the present invention, the average particle size is determined as the value of a median diameter (d=50) measured at a measurement temperature of 25° C.

(Anti-Thyroxine Antibody)

In the present invention, a thyroxine-binding substance is bonded to fluorescent particles and can be used to label thyroxine. As the thyroxine-binding substance, an anti-thyroxine antibody can be preferably used. As the anti-thyroxine antibody to be bonded to fluorescent particles, an antibody having specificity to thyroxine may be used. Examples of the anti-thyroxine antibody that can be used include an antiserum prepared from the blood serum of an animal that has been immunized with thyroxine, an immunoglobulin fraction purified from an antiserum, a monoclonal antibody obtainable by cell fusion using the spleen cells of an animal that has been immunized with cortisol, and fragments thereof [for example, F(ab')2, Fab, Fab', and Fv]. Preparation of these antibodies can be carried out by conventional methods. Furthermore, the antibody may be modified as in the case of a chimeric antibody or the like, and a commercially available antibody or an antibody prepared from an animal blood serum or a culture supernatant by a known method can also be used.

The antibody can be used without being restricted by the animal species or the subclass. For example, an antibody that can be used in the present invention is an antibody derived from an organism which can have an immune reaction, such as mouse, rat, hamster, goat, rabbit, sheep, cattle, or chicken, and specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, and bird IgY. These antibodies are applicable to both polyclonal and monoclonal antibodies. A fragmentized antibody is a molecule derived from a whole antibody, having at least one antigen binding site, and specific examples thereof include Fab and F(ab')2. These fragmentized antibodies are molecules obtainable by using an enzymatic or chemical treatment, or a genetic engineering technique.

Methods for immobilizing a binding substance such as an antibody or an antigen to particles are described in, for example, JP 2000-206115 A or the protocol attached to Fluo Spheres (registered trademark) Polystyrene Microsphere F8813 of Molecular Probe, Inc., and any known methods for preparing a reagent for immune agglutination can all be used. Furthermore, any principle for physical adsorption or chemical bonding by covalent bonding can be employed as the principle for immobilizing an antibody as a binding substance to particles. As a blocking agent which is used to cover the surfaces of particles that are not coated with an antibody after the antibody is immobilized to particles, any known substances, for example, bovine serum albumin (BSA), skimmed milk, casein, a soybean-derived component, a fish-derived component, polyethylene glycol, and commercially available blocking agents for immune reaction containing these substances or equivalent substances, can be used. These blocking agents can be subjected to a pretreatment such as partial modification by heat, an acid or an alkali as necessary.

A specific method for immobilizing an antibody to particles will be illustrated below. An antibody solution having the concentration adjusted to 0.01 mg/mL to 20 mg/mL is added to a liquid prepared by dispersing particles to a solids concentration of 0.1 mass % to 10 mass %, and the mixture is mixed. Stirring is continued for 5 minutes to 48 hours under the temperature conditions of 4° C. to 50° C. Subsequently, the particles are separated from the solution by centrifugation or any other method, and any antibody that is contained in the solution and has not been bound to the particles is sufficiently removed. Thereafter, an operation of washing the particles with a buffer solution is repeated 0 to 10 times. After the operation of mixing the particles and the antibody and causing the antibody to bind to the particles is carried out, it is desirable to protect the part on the particle surface that is not bound by the antibody, by using any component which does not participate in the antigen-antibody reaction, preferably a protein, and more preferably a blocking agent such as BSA (bovine serum albumin), Block-Ace, skimmed milk or casein.

When an antigen or an antibody is immobilized to particles, a stabilizer can be added as necessary. The stabilizer is not particularly limited so long as it is a compound which stabilizes an antigen or an antibody, such as sucrose or a synthetic or natural polymer such as a polysaccharide, and a commercially available product such as Immunoassay Stabilizer (Applied Biosystems, Inc.) can also be used.

(Measurement Method)

The measurement method of the present invention is construed by the broadest concept, including the detection of possible presence of cortisol and the measurement of the amount of cortisol (that is, quantification). A specific embodiment of the measurement method of the present invention may be a competition method.

In the competition method according to the present invention, first, a base plate for thyroxine immunoassay on which a conjugate of thyroxine or a derivative thereof and albumin having a thyroxine/albumin ratio of from 8 to 12 is immobilized, is brought into contact with anti-thyroxine antibody-labeled fluorescent particles and a test sample containing thyroxine. When thyroxine is not present in the test sample, an antigen-antibody reaction occurs on the base plate between the anti-thyroxine antibody-labeled fluorescent particles and the thyroxine on the base plate (that is, thyroxine in the conjugate of thyroxine or a derivative thereof and albumin). On the other hand, when thyroxine is present in the test sample, an antigen-antibody reaction occurs between the thyroxine in the test sample and the anti-thyroxine antibody-labeled fluorescent particles, and the antigen-antibody reaction between the anti-thyroxine antibody-labeled fluorescent particles and the thyroxine on the base plate (that is, thyroxine in the conjugate of thyroxine or a derivative thereof and albumin) is inhibited. After the reaction described above is completed, the anti-thyroxine antibody-labeled fluorescent particles that are not bound to the albumin on the base plate are removed. Subsequently, the extent of formation of an immune complex (that is, a complex between the anti-thyroxine antibody-labeled fluorescent particles and the thyroxine in the conjugate of thyroxine or a derivative thereof and albumin on the base plate) on the base plate is detected, and thereby the concentration of thyroxine in the test sample can be measured.

(Method for Detecting Fluorescence)

The method for detecting fluorescence in the present invention is not particularly limited, but for example, fluorescence intensity can be detected by using, for example, an instrument capable of detecting fluorescence intensity, specifically, a microplate reader or a biosensor for carrying out the detection of fluorescence caused by surface plasmon excitation (SPF). The detection method for fluorescence caused by surface plasmon excitation (SPF method) can make measurement with higher sensitivity than a detection method for fluorescence caused by epi-illumination excitation (hereinafter, referred to as "epi-illumination fluorescence method").

Regarding the surface plasmon fluorescence (SPF) biosensor, for example, a sensor described in JP 2008-249361 A, which includes a optical waveguide formed of a material which transmits excitation light having a predetermined wavelength; a metal film formed on one surface of this optical waveguide; a light source that generates a light beam; an optical system which causes the light beam to enter through the optical waveguide at an incident angle at which surface plasmon is generated with respect to the interface between the optical waveguide and the metal film; and a fluorescence detection means that detects the fluorescence generated as a result of excitation caused by the evanescent wave reinforced by the surface plasmon, can be used.

(Method for Measuring Amount of Test Substance)

According to an example of the method for quantitatively determining a test substance by the detection of fluorescence caused by surface plasmon excitation (SPF) according to the present invention, after the antigen-antibody reaction is completed after several minutes to several hours, the extent of formation of the immune complex is detected as fluorescence intensity. Thereby, the concentration of the test substance can be quantitatively determined from the relationship between fluorescence intensity and the concentration of the test substance. Furthermore, a test substance can be quantitatively determined by the following method. Specifically, samples containing a test substance at various known concentrations are prepared, and while the site for detecting fluorescence is washed down, the fluorescence signal from the fluorescence detection site is measured at plural different time points. From these plural measurement results, the change in the amount of fluorescence over time (gradient) against various concentrations of the test substance is determined. This change over time is plotted on the Y-axis, while the concentration of the test substance is plotted on the X-axis, and a calibration curve for the concentration of test substance against the change in the amount of fluorescence over time is obtained by using an appropriate fitting method such as the least squares method. With an optical signal system, the amount of test substance in a target test sample can be characterized based on calibration curves measured separately for different test substances.

A detection system for surface plasmon fluorescence (SPF) using the fluorescent particles of the present invention is an assay method for detecting fluorescence from a fluorescent substance depending on the amount of a test substance immobilized on a metal thin film on a base plate, and is a method different from a so-called latex agglutination method which detects the change in the optical transparency resulting from the progress of the reaction in a solution, for example, as turbidity. In the latex agglutination method, an antibody-sensitized latex in a latex reagent and the antigen in a specimen bind to each other through an antibody reaction, and agglutinate. This agglutinate increases with time, and a method of quantitatively determining the antigen concentration from the change in absorbance per unit time obtainable by irradiating near-infrared radiation to this agglutinate, constitutes the latex agglutination method. In the present invention, a detection method for a test substance, which is very simple compared to the latex agglutination method, is provided.

The present invention will be more specifically described by way of the following Examples, but the present invention is not intended to be limited by the Examples.

EXAMPLES

Example 1

1. Preparation of Powder of Thyroxine-Bovine Serum Albumin (T4-BSA) Conjugate-1

1-1. Synthesis of T4 Derivative

A T4 derivative 1 and a T4 derivative 2 were synthesized as illustrated in Scheme 1 below.

Thyroxine (T4, manufactured by Sigma-Aldrich Co.) was prepared, and a T4 derivative 1 was synthesized according to the synthesis method described in U.S. Pat. No. 4,040,907B. 270 mg of the T4 derivative 1 thus obtained was added to dimethylformamide (DMF; manufactured by Wako Pure Chemical Industries, Ltd.), and the derivative was dissolved while being stirred at room temperature. Thereafter, 285 mg of WSC (manufactured by Dojindo Laboratories Co. Ltd.) and 174 mg of NHS (manufactured by Wako Pure Chemical Industries, Ltd.) were added to the solution, and the mixture was stirred for 2 hours at room temperature. Thus, a T4 derivative 2 was synthesized.

1-2. Solution of T4-BSA Conjugate-1

Next, a conjugate (T4-BSA) of the T4 derivative 2 obtained in section 1-1. and bovine serum albumin (BSA) was prepared as illustrated in the following Scheme 2.

500 mg of bovine serum albumin (BSA, manufactured by Wako Pure Chemical Industries, Ltd.) was prepared and was dissolved in 100 mL of a 20 mM phosphate buffer solution (pH 7.0). The T4 derivative 2 synthesized in section 1-1. was dissolved in a DMF solution, and the solution was added to the phosphate buffer solution containing dissolved BSA. The mixture was stirred for 10 minutes. Thereafter, the mixture was left to stand for 12 hours, and the T4 derivative 2 was allowed to react with bovine serum albumin. After completion of the reaction, a white precipitate was removed by causing sedimentation by centrifugation (3,300 g, 30 min, 4° C.), and the supernatant liquid was collected. The collected supernatant liquid was filtered through a filter having a pore size of 0.22 μm, and thus a solution containing a T4-BSA conjugate-1 was obtained.

Scheme 1

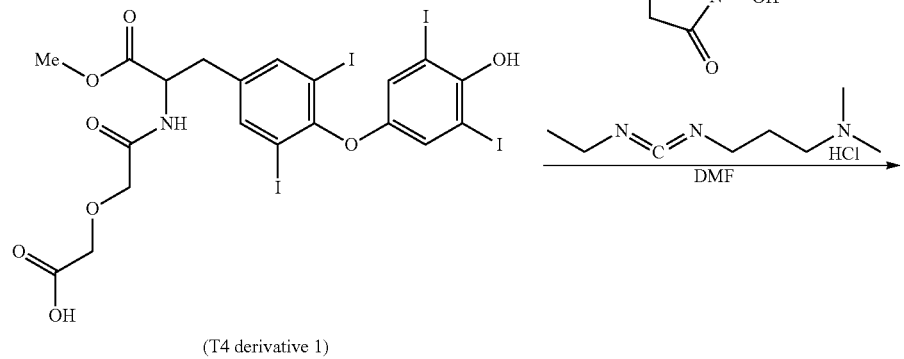

(T4 derivative 1)

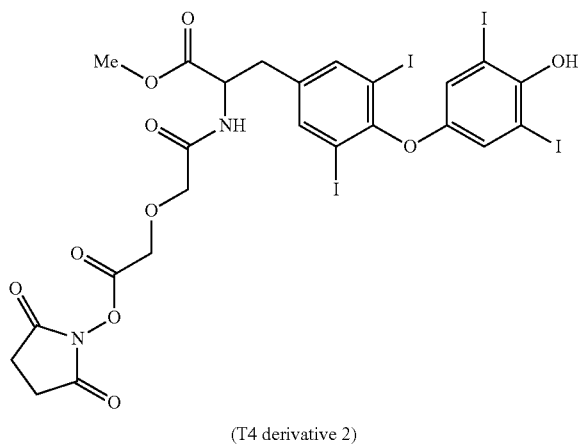

(T4 derivative 2)

Scheme 2

[Chem. 4]

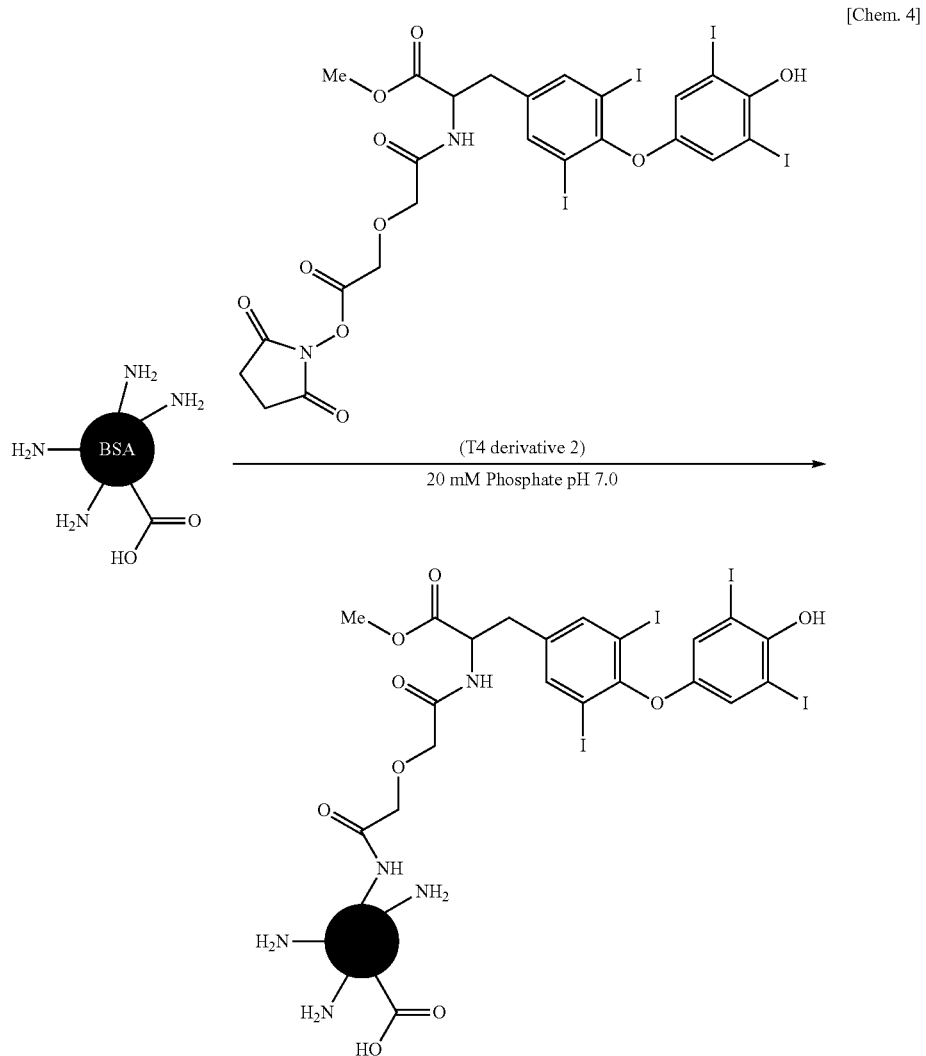

1-3. Purification of T4-BSA Conjugate-1 by Dialysis

Dialysis of the T4-BSA conjugate-1 solution obtained in section 1-2. was carried out by using a dialysis membrane tubing (product name: SnakeSkin Plated Dialysis Tubing, 10,000 MWCO, 22 mm×35 feet dry diameter; Product #68100; manufactured by Thermo Fisher Scientific, Inc.).

In a 5-L beaker, 5 L of a solvent mixture of ion-exchanged water ($H_2O$) containing 0.1 mass % trifluoroacetic acid (TFA, manufactured by Wako Pure Chemical Industries, Ltd.) and acetonitrile (AR) (1:1) was prepared. The pH of the solvent mixture was measured by using a reel type pH indicator paper manufactured by Tech-Jam Co., Ltd. (catalogue No. Product code No. KN3138095), and the pH value was 1. The solution of the T4-BSA conjugate-1 sealed in the dialysis membrane tubing was introduced into this solvent mixture, and the system was slowly stirred at room temperature.

1-4. Collection of T4-BSA Conjugate-1 White Solid by Lyophilization

Dialysis was carried out for 2 days, and then the aqueous solution in the dialysis tubing was collected. The collected aqueous solution was poured into a 500-mL pear-shaped flask, and the aqueous solution was lyophilized by using liquid nitrogen. Thus, about 400 mg of a white solid of the T4-BSA conjugate-1 was obtained as the conjugate of T4 and albumin of the present invention.

1-5. Preparation of Powders of T4-BSA (T4-Bovine Serum Albumin) Conjugate-2 to T4-BSA Conjugate-8

Preparation of powders of T4-BSA conjugate-2 to T4-BSA conjugate-8 was carried out by using the same preparation method in all cases, except that the masses of T4 and BSA used in the preparation of the T4-BSA conjugate-1 in section 1-1. were changed.

1-6. Analysis of Labeling Index of T4 to BSA (T4/BSA Ratio) in T4-BSA Conjugate

The number of T4 molecules bonded to one molecule of BSA was measured as the T4/BSA ratio.

The measurement was carried out by a MALDI-TOF-MS (hereinafter, indicated as MS) analysis. Sinapinic acid (manufactured by Sigma-Aldrich Co.) was used as the matrix. In a liquid mixture of water containing 0.1 mass % TFA and acetonitrile (1:1), sinapinic acid was dissolved to a concentration of 10 mg/mL to prepare a matrix solution. This matrix solution and an aqueous solution of T4-BSA (purified water) were mixed at 1:1 (5 μL each), and the mixture was sufficiently mixed in a microtube by using a pipette. Subsequently, 5 μL of the liquid mixture was dropped on the base plate of MS, the liquid mixture was naturally dried at room temperature, and an MS analysis was carried out. The measurement was carried out in a liner mode and a positive mode, and measurement was made by setting the molecular weight of mass detection to 60,000 to 100,000. The labeling index of T4 to BSA in the T4-BSA conjugate-1 to T4-BSA conjugate-8 thus obtained are shown in Table 1 as T4/BSA ratios.

TABLE 1

| Conjugate | T4 labeling index (T4/BSA ratio) |
|---|---|
| 1 | 5.4 |
| 2 | 9.4 |
| 3 | 9.8 |
| 4 | 10.6 |
| 5 | 10.9 |
| 6 | 11.1 |
| 7 | 11.4 |
| 8 | 16 |

2. Immunoassay of T4 Using Fluorescent Particles

Immunoassay of T4 was carried out as follows, by using the conjugate 1 to conjugate 8 prepared in section 1.

2-1. Preparation of Solution of T4-BSA Conjugates in Citrate Buffer Solution

150 μg each of the conjugate-1 to conjugate-8 prepared in section 1. was added to 1 mL of a citrate buffer solution (pH 5.2, 150 mM NaCl) to a concentration of 50 mM and dissolved, and thus a solution of a citrate buffer solution was obtained. When the labeling index of T4 to BSA increases, the solubility in the citrate buffer solution decreases, and thus a reliable solution cannot be prepared. The conjugate-8 having a T4/BSA ratio of 16 was found to have very poor solubility in the citrate buffer solution, and the conjugate could not be used in the subsequent evaluations.

2-2. Preparation of Fluorescent Particles Labeled with Anti-T4 Antibody

Fluorescent particles (particle size 260 nm) labeled with an anti-T4 antibody were prepared in the following manner.

250 μl of a 50 mM 2-morpholinoethanosulfonic acid (MES, manufactured by Dojindo Laboratories Co., Ltd.) buffer solution (pH 6.0) was added to 250 μL of an aqueous solution of fluorescent latex particles (product of Invitrogen, Inc.) having a solids concentration of 2 mass %, and 100 μL of 5 mg/mL anti-T4 monoclonal antibody (strain product of the company) was added thereto. The mixture was stirred for 15 minutes at room temperature. Thereafter, 5 μL of an aqueous WSC solution at 10 mg/mL was added thereto, and the mixture was stirred for 2 hours at room temperature. 25 μL of an aqueous solution of glycine (manufactured by Wako Pure Chemical Industries, Ltd.) at 2 mol/L was added thereto, and the mixture was stirred for 30 minutes. Subsequently, fluorescent latex particles were caused to sediment by centrifugation (15,000 rpm, 4° C., 15 minutes). The supernatant liquid was removed, and 500 μL of a phosphate buffered saline (PBS; manufactured by Wako Pure Chemical Industries, Ltd.) solution (pH 7.4) was added to the particles. The fluorescent latex particles were redispersed by using an ultrasonic cleaning machine. Centrifugation (15,000 rpm, 4° C., 15 minutes) was further carried out, the supernatant was removed, and then 500 μL of a PBS (pH 7.4) solution containing 1 mass % BSA was added to the particles to redisperse the fluorescent latex particles. Thus, a 1 mass % solution of anti-T4 antibody-bonded fluorescent latex particles was obtained.

2-3. Production of T4-BSA Conjugate-Immobilized Base Plate

A base of polymethyl methacrylate (PMMA) (manufactured by Mitsubishi Rayon Co., Ltd., Acrypet VH) was provided, a gold film having a thickness of 50 nm was deposited on one surface of the base by a vapor deposition method, and the gold film was cut to a width of 7 mm. Seven sheets of the same base plate were produced. Each of the solutions of T4-BSA conjugate-1 to T4-BSA conjugate-7 in citrate buffer solution prepared in section 1. was spot-applied on the gold-deposited surface of one of the base plates and dried. Thus, base plates 1 to 7 on which the T4-BSA conjugates were immobilized were produced.

2-4. Washing and Blocking of Base Plates

Before the base plates 1 to 7 produced as described above were attached to the flow channels of sensor chips, a PBS solution (pH 7.4)) containing Tween 20 (polyoxyethylene (20) sorbitan monolaurate, manufactured by Wako Pure Chemical Industries, Ltd.) at a concentration of 0.05 mass % was prepared in advance, and the base plates were washed repeatedly for 3 times by using 300 μL of this solution. After completion of washing, in order to achieve blocking of the T4-BSA conjugate-unadsorbed areas on the gold deposition film, 300 μL of a PBS solution (pH 7.4) containing 1 mass % casein (manufactured by Thermo Fisher Scientific, Inc.) was added to the base plates, and the base plates were left to stand for 1 hour at room temperature. After the base plates were washed with the washing solution, 300 μL of Immunoassay Stabilizer (manufactured by Applied Biosystems, Inc.) was added as a stabilizer, and the base plates were left to stand for 30 minutes at room temperature. The solution was removed, and moisture was completely removed by using a dryer.

2-5. Production of Sensor Chip

Flow channel type sensor chips were produced by encapsulating the 7 kinds of base plate thus produced in flow channels, so as to obtain the configuration of the second exemplary embodiment of JP 2010-190880 A.

3-1. Measurement

A test sample containing 1.3 μg/dL of thyroxine in blood serum and the anti-thyroxine antibody-labeled fluorescent particles were mixed in advance, and the mixture was spot-applied under various temperature conditions of 27° C., 30° C. and 33° C. The measurement area of the sensor chip was washed down at a flow rate of 10 μL/min while pump suction was carried out. The amount of fluorescence was obtained as signal values for a flow time of 10 minutes, the signal values were normalized with the signal values at 30° C., and the amount of fluorescence was plotted against temperature. The gradient of a straight line obtainable by the least squares method from three points of the plot was defined as the signal change rate (%/° C.). The various values of %/° C. with respect to the T4 labeling index (T4/BSA) are indicated in Table 2. Furthermore, the results obtained by plotting the T4/BSA ratio on the horizontal axis and plotting the signal change rate (%) on the vertical axis are shown in FIG. 1.

TABLE 2

| Conjugate | T4 labeling index (T4/BSA ratio) | Signal change rate (%/° C.) | |
|---|---|---|---|
| 1 | 5.4 | 7.35 | Comparative Example 1 |
| 2 | 9.4 | 4.72 | Invention Example 1 |

TABLE 2-continued

| Conjugate | T4 labeling index (T4/BSA ratio) | Signal change rate (%/° C.) | |
|---|---|---|---|
| 3 | 9.8 | 5.2 | Invention Example 2 |
| 4 | 10.6 | 5.8 | Invention Example 3 |
| 5 | 10.9 | 3.74 | Invention Example 4 |
| 6 | 11.1 | 5.5 | Invention Example 5 |
| 7 | 11.4 | 6.1 | Invention Example 6 |
| 8 | 16 | Undissolved | Reference |

As can be seen from the results indicated in Table 2, it was confirmed that the signal change rate caused by temperature change in immunoassay of T4 can be decreased by using the conjugate of T4 and BSA of the present invention having a ratio of thyroxine (T4) to albumin of from 8 to 12.

What is claimed is:

1. A base plate having a metal film on the surface for thyroxine immunoassay, comprising a conjugate of thyroxine and bovine serum albumin immobilized on said metal film on the base plate surface, the ratio of the molecule number of thyroxine or a derivative thereof to the molecule number of bovine serum albumin in the immobilized conjugate being from 9.4 to 11.4, and wherein said thyroxine is covalently conjugated with said bovine serum albumin through the amino group or carboxyl group of said thyroxine.

2. A method for measuring thyroxine in a test sample, the method comprising:
   (1) bringing the base plate for thyroxine immunoassay according to claim 1, into contact with anti-thyroxine antibody-labeled fluorescent particles and a test sample containing thyroxine; and
   (2) measuring the fluorescence based on the anti-thyroxine antibody-labeled fluorescent particles bound to the base plate.

3. The method according to claim 2, wherein in the step (2), fluorescence is measured by surface plasmon fluorescence measurement or epi-illumination fluorescence measurement.

4. The base plate for thyroxine immunoassay according to claim 1, the thickness of the metal film being from 0.1 nm to 500 nm.

5. The base plate for thyroxine immunoassay according to claim 1, the thickness of the metal film being from 1 nm to 200 nm.

* * * * *